(12) United States Patent
Anderson et al.

(10) Patent No.: US 6,939,453 B2
(45) Date of Patent: Sep. 6, 2005

(54) ELECTROPHORESIS PROCESS USING IONIC LIQUIDS

(75) Inventors: Norman G. Anderson, Rockville, MD (US); James A. Braatz, Beltsville, MD (US)

(73) Assignee: Large Scale Proteomics Corporation, Vacaville, CA (US)

( * ) Notice: Subject to any disclaimer, the term of this patent is extended or adjusted under 35 U.S.C. 154(b) by 10 days.

(21) Appl. No.: 10/218,111

(22) Filed: Aug. 14, 2002

(65) Prior Publication Data

US 2004/0031685 A1 Feb. 19, 2004

(51) Int. Cl.[7] .................... G01N 27/447; G01N 27/453; C07D 211/92

(52) U.S. Cl. ...................... 204/469; 204/451; 204/468; 204/466; 204/601; 204/616; 546/347

(58) Field of Search ................................. 204/451, 450, 204/456, 466, 468, 605, 601, 606, 455

(56) References Cited

U.S. PATENT DOCUMENTS

| | | | |
|---|---|---|---|
| 3,664,939 A | | 5/1972 | Luner et al. |
| 3,867,271 A | * | 2/1975 | Hoefer ....................... 204/456 |
| 3,888,758 A | | 6/1975 | Saeed |
| 3,951,777 A | | 4/1976 | Denckla |
| 4,088,561 A | | 5/1978 | Anderson |
| 4,702,814 A | | 10/1987 | Audeh |
| 4,747,919 A | | 5/1988 | Anderson |
| 4,886,866 A | | 12/1989 | Braatz et al. |
| 4,929,706 A | | 5/1990 | Heifetz et al. |
| 4,940,737 A | | 7/1990 | Braatz et al. |
| 5,039,458 A | | 8/1991 | Braatz et al. |
| 5,091,176 A | | 2/1992 | Braatz et al. |
| 5,169,720 A | | 12/1992 | Braatz et al. |
| 5,175,229 A | | 12/1992 | Braatz et al. |
| 5,403,750 A | | 4/1995 | Braatz et al. |
| 5,429,734 A | | 7/1995 | Gajar et al. |
| 5,431,817 A | | 7/1995 | Braatz et al. |
| 5,552,241 A | | 9/1996 | Mamantov et al. |
| 5,824,204 A | | 10/1998 | Jerman |
| 5,827,602 A | | 10/1998 | Koch et al. |
| 5,993,627 A | | 11/1999 | Anderson et al. |
| 6,255,504 B1 | | 7/2001 | Roberts et al. |
| 6,280,883 B1 | | 8/2001 | Lamanna et al. |
| 6,316,643 B1 | | 11/2001 | Roberts et al. |
| 6,326,104 B1 | | 12/2001 | Caja et al. |
| 6,350,721 B1 | | 2/2002 | Fu et al. |
| 6,365,301 B1 | | 4/2002 | Michot et al. |
| 2001/0031875 A1 | * | 10/2001 | Kitazume ................... 546/347 |
| 2003/0080312 A1 | * | 5/2003 | Seddon et al. ................. 252/1 |

FOREIGN PATENT DOCUMENTS

| | | | | |
|---|---|---|---|---|
| JP | 07-55769 A | * | 3/1995 | ......... G01N/27/447 |
| WO | WO 00/67009 A1 | * | 11/2000 | .......... G01N/27/26 |

OTHER PUBLICATIONS

JPO machine translation of 07–055769 A (Takafumi et al.).*
Staynov et al. ("Molecular Weight Determination of Nucleic Acids by Gel Electrophoresis in Non–aqueous Solution," Nature New Biology vol. 235 Jan. 26, 1972, pp. 108–110).*
Ivanov, "Rapid method for comparing the cytotoxicity of organinc solvents and their ability to destabilize proteins of the erythrocyte membrane," Pharmazie (2001), 56(10), 808–809).*
Abstract of Wasserscheid et al., "1–n–Butyl–3–methylimidazolium ([bmin]) octylsulfate—an even 'greener' ionic liquid," Green Chem., Aug. 8, 2002, 4(4) 400–404.*
David Bradley, "Greener ionic liquids," Reactive Reports Chemistry WebMagazine, issue #27, Oct. 2002.*
"Room Temperature Ionic Liquids", Rogers, Department of Chemistry, The University of Alabama, Sep. 6, 2001, http://bama.ua.edu/~rdrogers/ionicliquids.html.
"An Environmental Solution Ionic Liquids May Replace Hazardous Solvents", Renner, News Scan, John D. Holbrey and Kenneth R. Seddon *Queen's University Belfast*, Aug. 2001 Scientific News Scan American.
"New Horizons for Ionic Liquids Green 'Designer Solvents' Find Additional Effective Uses, New for Enzyme Catalysis and in Classic Organic Syntheses", Science/Technology, FREEMANTLE, C&EN, Jan. 1, 2001, pp. 21–25.
"Eyes on Ionic Liquids NATO Workshop Examines the Industrial Potential of Green Chemistry Using Room–Temperature 'Designer Solvents'", Science/Technology, FREEMANTLE, C&EN, May 15, 2000, p. 37.
"Room–Temperature Ionic Liquids: Neoteric Solvents for Clean Catalysis", SEDDON, The Queen's University of Belfast, School of Chemistry WWW Server, http://www.ch.qub.ac.uk/resources/ioni/review/review.html, Aug. 2, 2000.
"Capillary Electrophoretic Application of 1–Alkyl–3–methylimidazolium–Based Ionoic Liquids", Yanes et al., Anal. Chem. 2001, 73, 3838–3844, Aug. 15, 2001.
"Enrichment of Hydrophobic Proteins via Triton X–114 Phase Partitioning and Hydroxyapatite Column Chromatography for Mass Spectrometry", Wissing et al., Electrophoresis 2000, 21, 2589–2593, month of publn not known currently.
"Ionic Liquids as Electrolytes for Nonaqueous Capillary Electrophoresis", Vaher et al., Electrophoresis 2002, 23, 426–430, Feb. 18, 2002.

* cited by examiner

*Primary Examiner*—Alex Noguerola
(74) *Attorney, Agent, or Firm*—John E. Tarcza; John C. Robbins; Thomas Gallegos

(57) ABSTRACT

Highly hydrophobic compounds and hydrophobic proteins are solubilized in a non-aqueous solvent containing an electrolyte for electrophoretic separation. The non-aqueous solvent is an ionic liquid or a mixture of an organic solvent containing an ionic liquid in an amount to render the solvent electrically conductive and amenable for electrophoretic separation. The hydrophobic proteins are separated by electrophoresis using an electrophoresis gel that is compatible with the organic solvent and ionic liquid.

56 Claims, No Drawings

ELECTROPHORESIS PROCESS USING IONIC LIQUIDS

FIELD OF THE INVENTION

The present invention is directed to a process for processing, solubilizing or treating highly hydrophobic compounds, and particularly hydrophobic proteins with a non-aqueous liquid that is electrically conductive. The process can include electrophoretic separation of molecules, and particularly proteins, polypeptides and macromolecules using an ionic liquid as an electrolyte in an organic solvent. The invention is further directed to novel ionic liquids and to a process for making novel ionic liquids for solubilizing highly hydrophobic proteins and for the electrophoretic separation of molecules.

BACKGROUND OF THE INVENTION

Electrophoresis is a well known technique for separating complex organic molecules. In recent years, electrophoresis has been used extensively in the separation, isolation and analysis of proteins. Electrophoresis has the advantage of being able to separate a large number of proteins from a very small sample.

In the typical electrophoretic separation of macromolecules, such as nucleic acids and proteins, an electric potential is applied to opposite ends of a substrate that is in the presence of an electrolyte. The electric current causes the macromolecules to migrate through the medium along the substrate to a location determined by the size and charge of the molecules, the substrate retarding movement and the current. Typically, the electrolyte is an inorganic salt in an aqueous medium.

One type of electrophoresis process uses a capillary electrophoresis device. This device includes one or more capillary tubes or channels containing the electrolyte solution. An electric field is created in the electrolyte solution between the ends of the capillary to cause the macromolecules to migrate along the length of the capillary. The velocity of the sample component through the capillary tube is a function of the electric field, the movement of the carrier liquid and the electric mobility of the sample component. One example of a capillary electrophoresis device is disclosed in U.S. Pat. No. 6,159,353 to West et al.

Capillary electrophoresis devices are typically an enclosed capillary tube. The capillary tubes generally have a length of about 1 to 2 meters. The voltage of the electric current applied to the electrolyte solution can range from about 5 to 50 kilovolts. The separation of the constituents of the sample is the result of the differential migration through the gel or capillary tube due to the charge to size ratio or by chemical interactions between the samples and a stationary phase in the capillary or gel. The efficiency of the separation is enhanced by reducing the capillary diameter and the thickness of the gel.

Other types of electrophoresis separation processes use a gel supported in a tube. This electrophoresis separation is generally referred to as a first dimension separation when combined with an additional subsequent separation. The tube contains an electrophoresis gel where each end of the tube is immersed in an aqueous solution containing a buffer or other electrolyte. The gel is commonly an acrylamide gel that contains large amounts of water. A test sample is applied to one end of the tube and an electric potential is applied between opposite ends of the tube. The components of the test sample migrate along the length of the tube a distance according to the charge and mass of the component. When electrophoresis is performed in the presence of ampholytes, the components may focus based on charge alone.

Another electrophoresis process employs a gel slab or a thin planar gel. The gels generally have a length of about 5 to 100 cm. When preceded by a first dimensional separation, it is commonly referred to as second dimension electrophoresis. The gel slab is typically a sheet having a thickness of about 1 mm to 3 mm and is supported between two plates. Typically, the supports are two sheets of glass with spacers between the sheets to maintain a uniform spacing. Test samples can be applied to one end of the gel, in a discrete location or a tubular shaped gel containing separated molecules obtained from a first dimension electrophoresis separation process that has been separated from the tube. In other forms, liquid samples containing molecules to be separated are placed along a side edge of the gel slab or in wells. The ends of the gel slab are immersed in a buffer solution and an electric potential is applied to opposite ends to cause the molecules of the sample to migrate through the gel.

Electrophoresis is a particularly suitable technique for the separation and isolation of many proteins. The prior electrophoresis processes and devices use an aqueous system containing an electrolyte and where the gel material is formed by contacting the polymer and the aqueous system. The presently available electrophoresis systems are limited by the ability to solubilize the proteins in an aqueous medium using buffers, salts, denaturants, detergents or other solubilizing agents. Many proteins that are highly hydrophobic cannot be solubilized in aqueous systems, and thus, cannot be subjected to electrophoresis separation using conventional electrophoresis processes. If one uses a solubilizing agent which imparts a charge to the molecule, it may solubilize but loose its specific charge to size ratio and the basis for its separation ability during electrophoresis. Certain proteins under controlled conditions can be solubilized in organic solvents. However, the organic solvents are not compatible with the electrophoresis gels or the aqueous systems used to form the gel. The organic solvents are also not electrically conductive to be amenable to electrophoresis.

Efforts have been made to solubilize or suspend hydrophobic proteins in aqueous solutions for various processes. For example, Wissing et al. in "Enrichment of Hydrophobic Proteins via Triton X-114 Phase Portioning and Hydroxyapatite Column Chromatography for Mass Spectrometry", *Electrophoresis*, 2000, 21, 2589–2593 discloses the separation of hydrophobic membrane proteins. The process discloses forming an aqueous solution of the nonionic detergent Triton X-114, which at 20° C. separates into a detergent depleted phase and a detergent enriched phase. The detergent enriched phase is disclosed as containing the hydrophobic proteins. The proteins were separated by column chromatography, followed by electrophoresis using IPG strips. The gels were then stained, the spots excised and the peptides extracted for analysis by MALDI-TOF.

Low temperature molten salts are a class of salt compounds and compositions commonly referred to as ionic liquids. Ionic liquids are generally liquid at room temperature and are made up of organic cations and anions. Ionic liquids have been proposed for use as solvents, for catalysts, organic synthesis and non-aqueous batteries. Examples of electrochemical cells that include ionic liquids are disclosed in U.S. Pat. No. 5,552,241 to Manantov et al. and U.S. Pat. No. 6,326,104 to Caja et al.

Accordingly, a continuing need exists in the industry for improved processes for solubilizing hydrophobic compounds and the electrophoretic separation of these molecules.

SUMMARY OF THE INVENTION

The present invention is directed to compounds, compositions, methods and apparatus for the processing of macromolecules, and particularly proteins. In one embodiment, the invention is particularly directed to an electrophoretic separation process and to solvents and electrophoresis gels for the separation process.

Accordingly, a primary object of the invention is to provide a process for the electrophoretic separation of macromolecules, such as proteins in a non-aqueous system.

Another aspect of the invention is to provide a process for the electrophoretic separation of proteins and polypeptides using an ionic liquid.

Still another aspect of the invention is to provide an organic solvent capable of solubilizing hydrophobic compounds and contains an electrolyte in an amount to render the organic solvent electrically conductive. The electrolyte is preferably an ionic liquid that is miscible in the organic solvent and is compatible with the hydrophobic compound.

Another aspect of the invention is to provide a solution of highly hydrophobic compounds such as proteins in an electrically conductive nonaqueous liquid, which can include an ionic liquid.

A further aspect of the invention is to provide a process for the electrophoretic separation of hydrophobic molecules that are solubilized in an organic solvent. The invention is particularly suitable for the electrophoretic separation of highly hydrophobic proteins.

Another aspect of the invention is to provide a gel electrophoresis process for the electrophoretic separation of hydrophobic molecules where the electrophoresis gel is a non-aqueous gel. The gel is preferably a polymeric material that is able to form a stable gel in the presence of a non-aqueous liquid. In one embodiment of the invention, the non-aqueous liquid functions as a solvent or cosolvent for the material or composition being separated.

Still another aspect of the invention is to provide an electrophoresis gel for the electrophoretic separation of molecules where the gel is formed in the presence of a solvent. In one embodiment, the gel forming polymer is a urethane based polymer or a urea-urethane based polymer.

A further aspect of the invention is to provide a solvent system capable of solubilizing or dispersing hydrophobic compounds, such as hydrophobic proteins, where the solvent system includes an ionic compound in an amount sufficient to electrophoretically separate the hydrophobic compounds. The solvent system in one embodiment includes an organic solvent that is compatible with an electrophoresis gel and is able to solubilize the hydrophobic proteins. The solvent system also contains an amount of an ionic liquid to provide sufficient ionic character to the solvent system to enable the electrophoretic separation of the macromolecules or act as an electrolyte.

Another aspect of the invention is to provide an ionic liquid having a substituent group with detergent properties. In one embodiment, the ionic liquid includes a substituent of dodecylsulfate forming the anion of the ionic liquid.

Still another aspect of the invention is to provide a process of producing ionic liquids having detergent properties and are able to solubilize a variety of hydrophobic compounds.

The various aspects of the invention are basically attained by providing an electrophoresis separation process for separating a sample into its components. The electrophoresis gel is formed from a polymer and a first organic liquid. The gel has a first end, a second end and a sample at the first end of the gel. The first end and the second end of the gel are in contact with the first and the second organic liquid containing an electrolyte. The first and second organic liquids may be the same. An electric potential is applied between the first end and the second end of the gel to cause the components in the sample to migrate through the gel from the first end toward the second end thereby electrophoretically separating components of the test sample.

The aspects of the invention are also attained by providing a process for electrophoretic separation of proteins. An electrophoresis substrate is provided for the electrophoretic separation of molecules. The electrophoresis substrate has a first end and a second end that are in contact with a non-aqueous electrically conducting liquid. A protein sample is placed at the first end of the electrophoretic substrate. An electric current is applied between the first end and second end of the electrophoresis substrate to cause the proteins in the sample to migrate through the substrate and to electrophoretically separate the proteins.

The aspects of the invention are further attained by providing an electrophoresis gel substrate which comprises a polymeric gel material with a dimension sufficient to separate macromolecules by electrophoresis. An organic liquid is dispersed in the polymer gel material to form the gel substrate. The organic liquid contains an electrolyte in an amount sufficient to electrophoretically separate macromolecules through the gel. The organic liquid is compatible with the polymeric gel material to form a stable gel.

The aspects of the invention are still further attained by providing an ionic liquid having the formula

where $A^+$ is a cation selected from the group consisting of pyridinium, pyridazinium, pyrimidinium, pyrazinium, imidazolium, pyrazolium, thiazolium, oxazolium, triazolium, and derivatives thereof alone or in mixture with each other, and $Z^-$ is an anion having anionic surfactant properties, and where the ionic liquid is liquid at or near room temperature.

The various aspects of the invention are also attained by providing a separation process for separating hydrophobic constituents. A mixture of a sample and a solvent medium is formed. The sample contains the hydrophobic constituents and the solvent medium contains an organic solvent and an ionic liquid in an amount sufficient to render the mixture electrically conductive. The mixture is passed through a separation medium and separates the hydrophobic constituents in the separation medium.

These and other aspects of the invention will become apparent from the following detailed description of the invention which describes various embodiments of the invention.

DETAILED DESCRIPTION OF THE INVENTION

The present invention is directed to a process of solubilizing hydrophobic compounds in non-aqueous liquids, optionally followed by electrophoretic separation(s). The invention is also directed to a process and compound for solubilizing and separating hydrophobic macromolecules, such as proteins, in a sample.

A common process for separating macromolecules, complex organic molecules, nucleic acids, polysaccharides polypeptides and proteins is by electrophoresis. Derivatives of each of these such as glycoproteins, lipoproteins, peptide nucleic acids and various complexes are also separated by electrophoresis, and all may be separated by the present invention. Conventional electrophoresis requires solubilizing the sample to be separated in an aqueous medium containing an electrolyte. Sometimes, the aqueous medium includes a detergent, such a sodium dodecylsulfate (SDS), to assist in solubilizing the proteins. However, anything that imparts a charge may adversely affect separation by electrophoresis. Many proteins are highly hydrophobic and cannot be solubilized in an aqueous medium in amounts sufficient to be separated by electrophoresis. Certain proteins cannot be solubilized in an aqueous medium regardless of the type of detergent or other solubilizing agent. For example, membrane proteins cannot be solubilized in an aqueous medium, and thus, cannot be separated by the standard electrophoresis, which use an aqueous electrolyte system.

One aspect of the invention is to provide a process for solubilizing hydrophobic molecules, and particularly hydrophobic proteins, peptides and polypeptides in an electrically conducting liquid medium. Preferably, the liquid is a non-aqueous organic liquid that is able to solubilize or disperse highly hydrophobic proteins and contains an ionic component in an amount sufficient to render the liquid electrically conductive. In preferred embodiments of the invention, the liquid medium contains an ionic liquid in an amount sufficient to function as an electrolyte so that the resulting liquid medium is electrically conductive. As used herein, the term "solvent" and "solvent medium" are intended to refer to liquids that function as a solvent or cosolvent to solubilize a desired solute. The solutes of the process of the invention are primarily proteins including hydrophobic proteins, as well as complex organic molecules. It will be understood that the solvent medium is not limited to ionic liquids and the processes described herein are not limited to treating proteins. Any order of contacting sample with ionic liquid and optional solvent in such a system may be used. As used herein, the term "hydrophobic" refers to compounds that are not soluble in water at room temperature.

In a first embodiment of the invention, a solvent medium is prepared that is able to solubilize hydrophobic molecules and is amenable to electrophoretic processes so that the hydrophobic molecules can be separated and isolated. The invention is particularly directed to a solvent medium that is able to solubilize hydrophobic proteins, glycoproteins, lipoproteins, polypeptides and nucleic acids. The solvent medium to be amenable to electrophoresis processes contains a sufficient concentration of ionic species to render the solvent medium electrically conductive to be suitable for electrophoretic separation. The separation process can be carried out using any suitable separation medium. Examples of a suitable separation medium include a column, gel, capillary or array such as SELDI. In one embodiment, the hydrophobic compounds are separated by chromatography or any electrophoresis substrate such as capillary, zone or gel electrophoresis.

In one embodiment, the solvent medium includes an organic solvent that is liquid at or near room temperature. Preferably, the organic solvent is selected based on the properties of the solute so that the solute is sufficiently soluble in the solvent. The organic solvents can be hydrophobic or hydrophilic. An example of one suitable solvent is methylene chloride. Other suitable organic solvents include ethanol, methanol, methylsulfoxide, methylethylketone, acetone, polyethylene glycol, acetonitrile, benzene, octane, methanol 2-propanol, 1,2-dichloroethane, N,N-dimethylacetamide, dimethyl formamide, toluene, xylene, 1-methyl-2-pyrrolidone, N-ethyl naphthaline, trichloromethane, derivatives of any of these and mixtures thereof. Suitable solvents also include straight alkanes and alkenes, branched alkanes and alkenes and cyclic alkanes and alkenes, aryl compounds such as benzene and toluene, fused aromatic compounds, and bridged aromatic compounds, which can be substituted with one or more pendant groups.

A variety of organic solvents can be used depending on the solute and the ionic liquid. Preferably, the ionic liquid is compatible with the organic solvent and is readily miscible without phase separation or turbidity. The combination of the organic solvent and the ionic liquid are selected to provide the desired ionic conductivity of the solvent medium. Examples of suitable organic solvents include acetonitrile, propylene carbonate, diethyl carbonate, ethyl carbonate, ethyl methyl carbonate, benzonitrile, dimethyl formamide, sulfolane, tetrahydroformate, diethylether, dimethoxyethane, tetrahydrofuran, methyltetrahydrofuran, dibutyl carbonate, butyrolactones, benzonitrile, nitromethane, nitrobenzene, N-methylpyrrolidone, dimethylsulfone, tetramethylene sulfone, sulfolane, thiophene, alcohols, ketones and hydrocarbons of all types and derivatives of any of these solvents.

The solvent medium in one embodiment includes a mixture of an organic liquid and an ionic liquid that is soluble or miscible with the organic liquid. Generally, the organic liquid is not electrically conductive and is compatible with the ionic liquid. In one preferred embodiment where the solvent medium is suitable for the electrophoresis separation of proteins, the solvent medium contains an organic solvent and at least about 0.05% by volume and typically at least 0.1% by volume of an ionic liquid that is compatible and miscible with the organic solvent component. Typically, the solvent medium contains about 2.0% or less of the ionic liquid. The solvent medium generally contains about 0.05% to about 2.0%, and preferably about 0.1% to about 2.0% of an ionic liquid where the percentages are by volume. In one preferred embodiment, the solvent medium contains about 0.1% to about 2.0% by volume of an ionic liquid. In another embodiment, the solvent medium contains about 0.08% to about 0.12% of an ionic liquid with the balance being an organic solvent where the percentages are by volume. In other embodiments, the solvent medium can consist essentially of an ionic liquid. The important feature is that the amount of ionic liquid is sufficient to act as an electrolyte and render the liquid electrically conductive for electrophoresis. Typically, the solvent medium consists essentially of a non-electrically conductive organic solvent and an ionic liquid in an amount to render the solvent medium sufficiently electrically conductive for the intended purpose. The organic solvent can be a single solvent or mixture of solvents and cosolvents. Generally, it is not necessary to add other solubilizing agents such as detergents to the solvent medium although such solubilizing agents can be added as needed depending on the organic solvents in the system and solubility of the solute. The solute can be added directly to the organic solvent or the ionic liquid before the ionic liquid is mixed with the organic solvent. The solute can also be added directly to the mixture of the organic solvent and the ionic liquid.

Many proteins, polypeptides and other compounds are difficult to solubilize in organic solvents unless a counterion is provided to interact with the highly charged proteins. The ionic liquids of the invention have been found to provide an ionic species which act as a counterion to solubilize such compounds, particularly very hydrophobic proteins, such as membrane proteins.

Ionic liquids are ionic substances with melting points at or below room temperature. In recent years, there has been an increased interest in ionic liquids for their interest in chemical processes since ionic liquids have a variety of desirable properties. Ionic liquids have been proposed for catalysis for green technology, electrochemistry and some separations. Ionic liquids are benign, nonvolatile, nonflammable and have high thermal stability with very low or negligible vapor pressure. The ionic liquids are generally good solvents for a wide variety of both inorganic and organic materials. Some ionic liquids are miscible in water. The miscibility in water by the ionic liquid is generally dependent on the inorganic anion. For the purposes of this application, ionic liquids include compounds which are liquid at reasonable working temperatures where the solvent remains a liquid with acceptable vapor pressure. Ionic liquids also include ionic compounds which are liquid in a suitable solvent system, such as an organic hydrophobic solvent. A significant advantage of ionic liquids over other electrolytes is their solubility in non-aqueous liquids, such as those typically used to dissolve or suspend hydrophobic components in a sample.

Many ionic liquids are known, which provide flexibility in properties of the ionic liquid as a solvent. A common group of ionic liquids includes nitrogen-containing organic cations and inorganic anions. Bulky organic cations such as N-alkylpyridinium and 1-alkyl-3-methylimidazolium are combined with inorganic anions such as $Cl^-$, $Cl^-/AlCl_3$, $NO_3^-$, $PF_6^-$ (HFP) and $BF_4^-$ (TFB). Other suitable anions include bis(trifluoromethanesulfonyl) imide $(CF_3SO_2)_2N^-$ and trifluoromethanesulfonate $(CF_3SO_3^-)$. The various combinations of the anions and cations provide a large selection of ionic liquids depending on the separation process and the properties of the composition being processed. The ionic liquids of the invention can be hydrophobic or hydrophilic.

The ionic liquids of the invention have the general formula (1)

$$A^+X^- \qquad (1)$$

where $A^+$ is an organic cation and $X^-$ is an anion and the compound of formula (1) is liquid at room temperature. $A^+$ and $X^-$ can be any suitable cation and anion, respectively, that are able to form an ionic liquid that is liquid at or near room temperature.

Examples of suitable cations include pyridiniums, pyridaziniums, pyrimidiniums, pyraziniums, imidazoliums, pyrazoliums, thiazoliums, oxazoliums and triazoliums and derivatives thereof having the formulas:

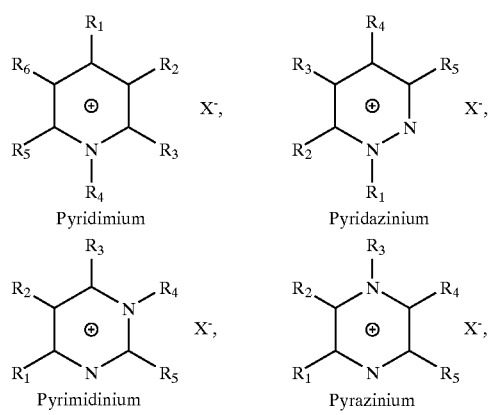

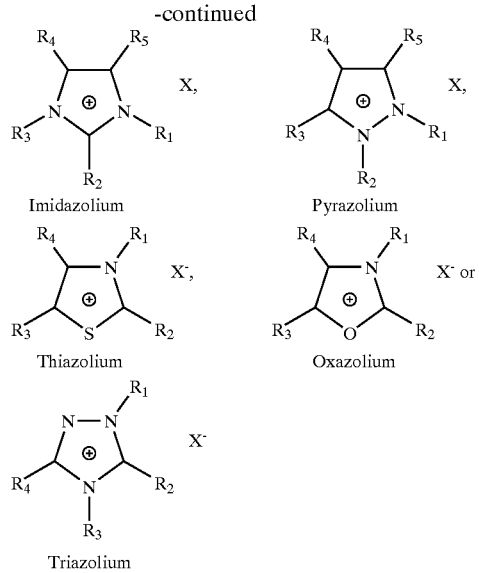

where $R_1$, $R_2$, $R_3$, $R_4$, $R_5$ and $R_6$ are an organic radical, which can be the same or different and are selected according to the desired properties of the ionic liquid. In one embodiment of the invention, $R_1$, $R_2$, $R_3$, $R_4$, $R_5$ and $R_6$ are selected from the group consisting of hydrogen, halogen, and alkyl. The alkyl is generally a lower alkyl group and preferably has 1–4 carbon atoms. The alkyl group can be straight chain or branched and include one or more substituents and pendant groups. A large number of other substituents may also be present. In other embodiments, the R groups provide surfactant properties to the cation. The alkyl group can be substituted with a halogen such as chlorine or fluorine, —$CF_3$, —$SF_5$, —$CF_3S$, —$SCH(CF_3)_2$ or —$CS(CF_3)_3$. In one embodiment, the cation is selected from the group consisting of N-alkylpyridinium and 1-alkyl-3-methylimidazolium where the alkyl has 1–4 carbon atoms.

The anion $X^-$ can be selected from any suitable anion that has an affinity for the cation so that the resulting compound is liquid and stable at room temperature. Examples of suitable anions include mono or diperfluoro sulfonate, $(CF_3)_2PF_4^-$, $(CF_3)_3PF_3^-$, $(CF_3)_4PF_2^-$, $(CF_3)_5PF^-$, $(CF_3)_6P^-$, $SF_5CF_2SO_3^-$, $SF_5CHFCF_2SO_3^-$, $SF_3CF_2(CF_3)_2CO^-$, $(CF_3SO_2)CH^-$, $(SF_5)_3C^-$, $(O(CF_3)_2C_2(CF_3)_2O)_2PO^{3-}$, and —$N(SO_2CF_3)_2$. In other embodiments, the anion can be a halide, such as $Cl^-$ or $F^-$, $BF_4^-$, $PF_6^-$, $AsF_6^-$, $CF_3SO_3^-$, $NO_3^-$, $AlCl_4^-$ and $Al(OH)_2Cl_2^-$. Iron (III) chlorides can also be used as a suitable anion.

Examples of particularly suitable cations include 1-ethyl-3-methylimidazonium, 1,2-dimethyl-3-propylimadozolium imide, n-butylpyridinium imide, 1-propyl-3-methylimidazolium, perfluoro-1-ethyl-3-methylimidazolium imide, and 1-butyl-3-methylimidazolium. Other suitable ionic liquids are disclosed in U.S. Pat. No. 5,827,602 to Koch et al., U.S. Pat. No. 6,350,721 to Fu et al., U.S. Pat. No. 6,326,104 to Caja et al. And U.S. Pat. No. 5,552,241 to Mamantov et al., which are hereby incorporated by reference in their entirety.

In one preferred embodiment, the ionic liquid is selected from the group consisting of 1-butyl-3-methylimidazolium hexafluorophosphate, 1-butylpyridinium nitrate, 1-ethyl-3-methylimidazolium bis(trifluoromethanesulfonyl) imide, 1,2-dimethyl-4-fluoropyrazolium tetrafluoroborate, 1-ethyl-2-methylpyrazolium tetrafluoroborate and N-butylpyridininium hexafluoroborate.

In one preferred embodiment, the ionic liquid has the formula

$$A^+Z^- \qquad (2)$$

where $A^+$ is as defined above and $Z^-$ is an anion that has detergent properties. The anion can be organic or inorganic. Preferably, $Z^-$ is the anion of an anionic detergent, which has a hydrophilic group and a hydrophobic group. $A^+$ is a cation having the structure defined above. $Z^-$ in one embodiment has the formula

$$YR_7^- \qquad (3)$$

where Y is an anionic group and $R_7$ is an alkyl or alkenyl group having about 6 to about 22 carbon atoms, and preferably about 10 to about 22 carbon atoms. Y is selected from the group consisting of $-SO_4^-$, $-PO_4^-$ and $-CO_2^-$. In one preferred embodiment, $Z^-$ is selected from the group consisting of dodecylsulfate and decylsulfate. Examples of ionic liquids having detergent properties include 1-ethyl-3-methyl-1H-imidazolium dodecyl sulfate and N-ethylpyridinium dodecylsulfate.

The ionic liquids can be produced by various processes. In one preferred process, the ionic liquid is prepared by combining an anionic detergent $Me^+Z^-$ where $Me^+$ is a metal cation, such as sodium dodecylsulfate and an ionic liquid having the formula $A^+X^-$ as defined above. Preferably, the ionic liquid and the anionic detergent are dispersed in a suitable organic solvent, such as acetone. The cation $Me^+$ of the anionic detergent and the anion $X^-$ of the ionic liquid form an insoluble compound, which precipitates from the mixture to produce an anionic liquid of $A^+Z^-$. In preferred embodiments, the anionic detergent and the ionic liquid are selected such that the cation of the anionic detergent and the anion of the starting ionic liquid precipitate as an insoluble metal salt from the reaction mixture. The cation $Me^+$ of the anionic detergent is preferably a metal ion such as sodium and potassium ions and the anion of the starting ionic liquid is preferably a halide such as a chloride anion, although other cations and anions can be used. The salt being formed is generally insoluble in the organic solvent to aid in separation. The resulting salt, such as NaCl or KCl, precipitates and is filtered. The solvent is then removed from the mixture by evaporation, for example, by a rotary evaporator, to obtain the ionic liquid. The liquid can be filtered through activated charcoal to further purify the resulting ionic liquid.

The resulting ionic liquids are particularly amenable to the separation of hydrophobic compounds, and particularly, proteins. The membrane proteins can be solubilized in the ionic liquid and then processed to separate and isolate the proteins by passing the mixture through a separation medium. In one embodiment, the hydrophobic proteins are separated by capillary electrophoresis. The capillary electrophoresis apparatus can be a standard assembly as known in the art. Several commercially available electrophoresis devices are available that are suitable for use in this invention for the separation of the hydrophobic proteins. Examples of suitable commercially available devices include the Bio-Rad BioFocus 2000 and the BioRad BioFocus 3000 by Bio-Rad Laboratories Inc., Hercules, Calif. These devices provide an automated capillary electrophoresis system having a UV detector and is operable with a computer. The electrophoresis system includes a base fused-silica capillary having an inner diameter of 50 $\mu$m and a total length of 50 cm–60 cm.

Likewise, ionic liquid detergents, alone or more commonly in mixture with non-aqueous solvents are useful to solubilize compounds for non-electrophoresis purposes including electroplating, fuel cells, electrolytic chemical reactions, cleaning solutions, particularly electro-enhanced cleaning, descaling, non-electroplating coating, coating or laminating organic ions, membrane-metal electrode connections and electrode formation, redox reactions, stabilizer for plastics and emulsifier in electric environments, prevention of electrode fouling and as solvents for chemical reactions, etc. In each situation, the ionic liquid detergent is acting both to help the solubilizing agent and to provide an electrolyte.

In another embodiment, the solvents containing an ionic liquid are used to separate proteins and particularly hydrophobic proteins by ion exchange or column chromatography. The hydrophobic proteins, such as membrane proteins, are acidified in an aqueous medium at about pH 2.5 or less so that the proteins carry only a positive charge. An excess of the ionic liquid is then added while maintaining the pH 2.5 or less. Generally, about a 100-fold excess of the ionic liquid is added to solubilize the protein into the ionic liquid. The protein is then exchanged into an aqueous medium by size exclusion chromatography or by dilution and repeated concentration. This results in a salt where the protein is the cation complexed with negatively charged ionic liquid component. The resulting preparation is then lyophilized and the protein complex with the negatively charged ionic liquid component is dissolved in an organic solvent such as methylene chloride. A negatively charged ion exchange support complexed with a positively charged ionic liquid component is prepared. The ionic liquid in the ion exchange column is replaced with the organic solvent and the protein complex is passed through the column. The proteins are then eluted from the column using the ionic liquid. Suitable ion exchange materials include a hydroxyapatite column.

In one embodiment of the invention, the solvent medium is a mixture of an organic liquid and an amount of an ionic liquid as defined above to provide the desired electrical conductivity. The solvent medium and the protein sample are passed through the separation medium. Electrophoresis separation of the solute can be carried out in a solvent medium that contains primarily an organic solvent that is able to solubilize the material to be separated and an amount of an ionic liquid to render the solvent medium sufficiently electrically conductive for the electrophoresis separation process. For electrophoresis separation, it has been found that an organic solvent containing 2.0% or less is sufficiently electrically conductive for electrophoresis. While a higher concentration is acceptable, the relative costs of solvent and ionic liquid suggest the use of a greater proportion of organic solvent.

In other embodiments of the invention, the electrophoresis separation process can be a gel electrophoresis process using a gel that is compatible with the solvent medium. Gel electrophoresis is particularly suitable for separating and isolating hydrophobic proteins, and particularly membrane proteins. The gel electrophoresis process can be a simple electrophoresis separation or in combination with a second dimension electrophoresis or other separation process.

Conventional gel electrophoresis typically includes a an electrophoresis gel shaped in elongated or rod-like fashion or as a thin slab. The gel may be supported by a tube or plate. At least the opposite ends of the gel are contacted with an aqueous buffer solution. The sample to be processed is placed at one or more locations in or on the gel and an electric potential is applied to the opposite ends, which cause the macromolecules in the sample to migrate through the gel.

A conventional electrophoresis gel is an acrylamide gel. Agarose, starch, cellulose, gelatin and various derivatives have also been used for electrophoresis. Conventional gel electrophoresis is performed in an aqueous medium with dissolved electrolytes to conduct electricity. However, many hydrophobic compounds which one may want to separate by electrophoresis are not soluble in aqueous mediums. Likewise for compounds labile in aqueous mediums. While an organic solvent frequently dissolves such compounds, organic solvents are incompatible with many conventional electrophoresis gels. Furthermore, organic solvents generally do not conduct electricity well and do not dissolve most conventional electrolytes. Out of these contradictory problems, the present invention was developed.

The gel electrophoresis process in this embodiment uses a polymeric gel material that is compatible with an organic solvent and an ionic liquid. In one preferred embodiment, the electrophoresis process uses a non-aqueous system.

The electrophoresis gels are able to form a gel substantially in the absence of water. Examples of suitable gels include polyurethane gels, polyisocyanates and polyurea-polyurethanes. The non-aqueous gels can be prepared by forming the hydrogel in water and then removing the water by evaporation. The polymer gel is re-formed with a suitable non-aqueous solvent medium. Alternatively, the non-aqueous gel can be formed by dissolving the polymer in a non-aqueous solvent and allowing the polymer to gel. In another embodiment, the prepolymer or monomers are polymerized in an non-aqueous solvent to form a gel followed by removal of that solvent and replacing it with a different solvent. In preferred embodiments where the gel is to be used for electrophoresis separation, the non-aqueous solvent includes a mixture of an organic liquid and an ionic liquid.

The polymers for forming the non-aqueous gel are prepared from prepolymers that are crosslinked with a suitable crosslinking agent. In one embodiment, the prepolymers are prepared from monomers of oxyethylene-based alcohols having the hydroxyl groups capped with polyisocyanate groups. The prepolymer can be modified with a compound having a first functional group which is reactive with the isocyanate. The modifying compound has a second functional group that is non-reactive with the isocyanate group of the prepolymer.

In one embodiment, the gels are formed from prepolymers of oxyethylene diols or polyols having a weight average molecular weight of about 7000 to about 30,000 where the hydroxyl groups are capped with polyisocyanate. The prepolymers are generally prepared by reacting the diol or polyol with polyisocyanate in an isocyanate-to-hydroxyl ratio of about 1.8 to about 2.2.

The diols and polyols are predominantly polyoxyalkylene diols or polyols made from ethylene oxide units. In other embodiments, the diol or polyol can include propylene oxide or butylene oxide units.

The gels suitable for use in forming the electrophoresis gels can be made from commercially available prepolymers sold under the trademark HYPOL by Dow Chemical Company, Midland, Mich. Examples of suitable prepolymers for forming the non-aqueous electrophoresis gels are disclosed in U.S. Pat. No. 4,886,866, U.S. Pat. No. 4,929,706, U.S. Pat. No. 4,940,737, U.S. Pat. No. 5,039,458, U.S. Pat. No. 5,091,176, U.S. Pat. No. 5,175,229, U.S. Pat. No. 5,169,720, U.S. Pat. No. 5,403,750 and U.S. Pat. No. 5,431,817, which are hereby incorporated by reference in their entirety.

The electrophoresis gels are preferably prepared substantially in the absence of water. A prepolymer is dispersed in an organic solvent such as methylene chloride or ethylene chloride to form a stable solution or dispersion. Typically, the prepolymer is a polyurethane or polyurea-urethane available under the HYPOL trademark by Dow Chemical Co. A solution of a crosslinking agent is then prepared preferably in the same organic solvent and mixed with the prepolymer solution. Preferably, the amount of the crosslinking agent added to the prepolymer is calculated to provide sufficient crosslinking to form stable gel.

The concentration of the prepolymer and crosslinking agent can be selected to provide the desired gelling and the rate of polymerization. It has been found that more dilute solutions of the prepolymer and the crosslinking provide a slower polymerization rate and a greater working time before gelling. Typically, the prepolymer is dispersed in the organic solvent to provide a concentration of 15% or less by volume and preferably about 10% or less by volume. The crosslinking agent is also dispersed in the organic solvent to provide a concentration of 15% or less, and preferably 10% or less by volume. The polymerization rate can also be reduced by cooling the reaction mixture below room temperature to extend the working life of the mixture.

In one preferred embodiment, the nonaqueous electrophoresis gel is produced by dissolving or dispersing the prepolymer in a suitable organic solvent containing an ionic liquid in an amount to render the organic solvent electrically conductive. The mixture is then crosslinked with a crosslinking agent such as a diamine. Particularly preferred diamine crosslinking agents are ethylene diamine and polyoxyalkylenediamines. Examples of this type of crosslinking agent are available from Huntsman Performance Chemicals, Huntsman Chemicals, Houston, Tex., sold under the trademark JEFFAMINE series. An example of a suitable crosslinking agent is a polyoxypropylenediamine sold under the trademark JEFFAMINE D-2000. Other suitable crosslinking agents include JEFFAMINE D-230 and JEFFAMINE D-400.

The prepolymer is mixed with the crosslinking agent and placed in or on a suitable support for the electrophoresis process. In one embodiment, the mixture is placed in an electrophoresis tube and allowed to gel. The gelled polymer in the electrophoresis tube is capable of conducting a first dimension electrophoresis separation. In another embodiment, the mixture is placed between two glass sheets and allowed to gel to form a gel slab. The resulting gel slab can be used for a first dimension or a second dimension electrophoresis separation of a sample.

The electrophoresis separation in one embodiment is preferably carried out substantially in the absence of water. The electrolyte is preferably an ionic liquid or an organic solvent containing an effective amount of an ionic component to render the organic liquid electrically conductive. The electrophoresis apparatus can have any suitable structure capable of separating the molecules of the sample by electrophoresis. One suitable example of a device for a first dimension gel electrophoresis separation is disclosed in U.S. Pat. No. 4,747,919 to Anderson, which is hereby incorporated by reference in its entirety. A suitable electrophoresis device for a gel slab is disclosed in U.S. Pat. No. 4,088,561 to Anderson, which is hereby incorporated by reference in its entirety. The compounds of the sample are separated by the electric potential applied between the ends of the gel. The gel spots containing the separated compounds are cut from the gel and the compounds are isolated from the gel using various processes as known in the art. Other suitable electrophoresis devices and methods are disclosed in U.S. Pat. No. 3,664,939 to Lunner, U.S. Pat. No. 3,888,758 to Saled, U.S. Pat. No. 3,951,777 to Denckla, U.S. Pat. No. 4,702,814 and U.S. Pat. No. 5,993,627 to Anderson et al, which patents are hereby incorporated by reference in their entirety.

The separation process of the invention separates the molecular components of a sample in a separation medium in the presence of an electrically conductive hydrophobic solvent medium. The solvent medium preferably includes a hydrophobic organic solvent and an ionic liquid in an amount to render the solvent medium electrically conductive. In one embodiment, the process is a capillary electrophoresis having one or more capillary tubes or channels. The sample is generally placed at one end with the ends of the capillary device in contact with the electrically conductive solvent medium. An electric potential is applied to the ends of the capillary device, which causes the molecules to separate along the length of the device.

In another embodiment, the separation process is a gel electrophoresis substrate, such as a polymeric gel substrate. The polymeric gel substrate is a gel formed in the presence of a solvent medium. Preferably, the solvent medium is an organic solvent containing an electrolyte such as an ionic liquid in an amount to render the solvent medium and the gel electrically conductive to be amenable for electrophoretic separation of a sample. The resulting electrophoresis gel substrate can be supported in a tube or between two plates to define a gel slab. The gel substrate has a dimension sufficient for electrophoretic separation of the sample. The opposition ends of the electrophoresis gel substrate are contacted with the electrically conductive solvent medium and an electric potential is applied along the substrate. A sample is typically provided at one end of the gel substrate. The electric potential is applied for the electrophoretic separation of the molecules in the sample.

The sample material generally contains hydrophobic proteins, which are separated by the electrophoresis process of the present invention. Typically, the hydrophobic proteins are membrane proteins and other strongly hydrophobic proteins. In one embodiment, the protein sample is a protein extract from the lipid layer of biomembranes. Such proteins typically form multiprotein complexes that are phosphorylated and/or glycosylated.

The following non-limiting examples are provided to demonstrate various embodiments of the invention.

EXAMPLE 1

This example demonstrates the formation of a non-aqueous electrophoresis gel.

A polyurethane prepolymer was obtained from Dow Chemical Co. under the trademark HYPOL G-50 and 1 part by volume (3.2 g) was combined with 6 parts by volume water (19.2 g). The components were mixed well and allowed to polymerize. The resulting gel was allowed to dry over several days in air at room temperature.

A first sample of the dried gel (0.5446 g) was covered with ethylene chloride in a closed container and allowed to stand overnight at room temperature. The resulting gel was clear, soft and pliable. The gel was weighed (6.18 g) which demonstrated an increase in weight of 11.3 fold.

EXAMPLE 2

A polyurethane electrophoresis gel was prepared in the absence of water in this example.

A 50% solution of HYPOL G-50 from Dow Chemical Co. was obtained in methylene chloride. A 50% v/v solution was prepared from 0.5 ml (0.45 g) of ethylenediamine and 0.5 ml of methylene chloride. 1.0 ml of the 50% solution of the prepolymer G-50 was mixed with 28.3 µl of the 50% solution of ethylenediamine. The resulting mixture gelled immediately.

EXAMPLE 3

The solution of the prepolymer G-50 of Example 2 was diluted with dry methylene chloride to obtain a 15% wt/vol concentration. The solution of the ethylenediamine was diluted with dry methylene chloride to obtain a 10% solution. 21 µl of the 10% ethylenediamine solution was combined with 1 ml of methylene chloride. Thereafter, 1 ml of the 15% solution of the prepolymer G-50 was added. The resulting mixture polymerized in about 1-2 minutes to produce a clear gel with no water and no bubbles.

EXAMPLE 4

In this example, an electrophoresis gel was prepared containing an ionic liquid.

A mixture was prepared from 21 µl of the 10% solution of ethylenediamine prepared in Example 3, 1 ml of dry methylene chloride and 40 µl of 1-ethyl-3-methyl-1H-imidazolium trifluoromethane sulfonate (EMITMS). To the mixture was added 1 ml of a 15% solution in methylene chloride of HYPOL G-50 (Dow Chemical Co.). The mixture was placed between two glass plates separated by 2 mm spacers. The mixture gelled in about 2 minutes to form a clear gel.

EXAMPLE 5

1 ml of a 15% solution of HYPOL G-50 in methylene chloride as prepared in Example 3 was combined with 1 ml methylene chloride and 65 µl of JEFFAMINE D-2000 from Huntsman Chemical Co. The JEFFAMINE D-2000 was a polypropyleneoxide diamine having a molecular weight of 2000. The resulting mixture formed a clear gel in about 2 minutes.

EXAMPLE 6

Conductivity measurements were made on various liquids and gels for the purposes of finding conditions appropriate for performing electrophoresis. The following results were measured in micro ohms. The last row is a conventional electrophoresis tank buffer.

| Sample | Reading |
|---|---|
| Distilled water | 0.83 |
| methylene chloride | 0.00 |
| $CH_2Cl_2$ + $dH_2O$ | 1.23 |
| G-50 + $Et(NH_2)_2$ | 8 |
| G-50 + $Et(NH_2)$ + EMITMS | 700 |
| Tris/Glycine/SDS + $H_2O$ | 745 |

The following measurements were based on 25 ml solvent alone and with 0.5 ml 1-ethyl-3 methyl-1H-imidazolium trifluoro methane sulfonate.

| Solvent | Solvent alone reading | solvent + EMITMS |
|---|---|---|
| Ethanol | 0.46 | 2950 |
| Methyl sulfonate | 3.87 | 4900 |
| Acetone | 0.18 | 17280 |
| Methylene chloride | 0.01 | 718 |
| PEG-400 | 0.23 | 65.3 |
| Acetonitrile | 0.24 | 35200 |
| 2-propanol | 0.03 | 651 |
| 1,2 dichloro ethane | 0.02 | 712 |

-continued

| Solvent | Solvent alone reading | solvent + EMITMS |
|---|---|---|
| Dimethyl formamide | 0.53 | 12440 |
| N-ethyl morpholine | 0.06 | 2.13 |
| Methanol | 0.68 | 15620 |
| Methyl ethyl ketone | 1.01 | 7150 |
| N,N-dimethyl acetamide | 373 | 8440 |
| 1-methyl-2-pyrrolidinone | 7.67 | 3260 |

Rhodamine labeled proteins from red blood cell ghosts were spotted on filter papers and various solvents were applied to show that the proteins were soluble because of fluorescence moving from the spot. The same solvents were tested in 2% ionic liquid to again determine solubility. Essentially all of the proteins were insoluble in water and soluble in a number of organic solvents, with and without the ionic liquid.

EXAMPLE 7

A transparent polyurethane gel was prepared by cross-linking Hypol G-50 Prepolymer with Jeffamine D-2000 (polyoxypropylenediamine) in methylene chloride according to Example 5 except for adding 50 μl of the ionic liquid 1-ethyl-3-methyl-1H-imidazolium trifluoromethane-sulfonate (EMITMS). The gel was cast in an all glass U-tube and attached with electrodes to a power supply. A sample of Rhodamine-labeled water insoluble red blood cell ghost membrane proteins were applied to the top of both sides of the U-tube, since it was unknown in which direction the proteins would migrate. After several hours of electrophoresis, a band of fluorescent material could be visualized entering the gel on one side, while a broad streak of material appeared to enter the opposite.

EXAMPLE 8

A surfactant ionic liquid was prepared when sodium dodecylsulfate and 1-ethyl-3-methyl-1H-imidazolium chloride were mixed together in acetone. A white precipitate formed and was filtered out. The white precipitate was believed to be sodium chloride. Acetone was vacuum evaporated yielding 1-ethyl-3-methyl-1H-imidazolium dodecylsulfate. The process was repeated using N-ethylpyridinium chloride as the ionic liquid to yield N-ethylpyridinium dodecylsulfate.

These surfactant ionic liquids in an organic solvent, such as methylene chloride, were effective in both solubilizing hydrophobic proteins which were previously insoluble in water, denaturants and surfactants. The resulting solubilized hydrophobic proteins were then electrophoresed according to the system in Example 7.

EXAMPLE 9

The 1-ethyl-3-methyl-1H-imidazolium dodecylsulfate surfactant ionic liquid of Example 8 was used as a solubilizing agent for peptides and to prevent matrix crystals in a MALDI application. A solution of 50% acetonitrile solvent with 50% 1-ethyl-3-methyl-1H-imidazolium dodecylsulfate is saturated with alpha hydroxy cinnomonic acid. A mixture of peptides from a trypsin digested protein is dissolved into the solution and the resulting liquid is spotted on a MALDI sample plate and allowed to dry. The spot remains liquid and crystals did not form. The MALDI sample plate is inserted into a mass spectrometer and the molecular masses of the peptides determined. Data is obtained without the laser hitting a crystal.

While various embodiments have been selected to illustrate the invention, it will be understood by those skilled in the art that various changes and modifications can be made without departing from the scope of the invention as defined in the appended claims.

What is claimed is:

1. An electrophoresis separation process for separating a sample into its components, said process comprising the steps of:

providing an electrophoresis gel comprising a polymeric gel material having a dimension sufficient to separate molecules and having a first end and a second end, a sample in contact with said gel, a first electrically conductive organic liquid at said first end, a second electrically conductive organic liquid at said second end, and applying an electric potential between said first end and said second end of said gel to cause said components in said sample to migrate through said gel from said first end toward said second end and electrophoretically separating components of said sample, wherein the electrophoresis gel is a polyurethane or polyurea-urethane based gel and said first organic liquid is compatible with said polyurethane or polyurea-urethane, and wherein said first and second organic liquids include at least one organic solvent selected from the group consisting of alcohols, ketones, nitriles, alkanes, alkenes, cycloalkanes, cycloalkenes, aromatic compounds, heterocyclic compounds, and mixtures thereof.

2. The process of claim 1, wherein said first and said second organic liquids include an ionic liquid in an amount sufficient to render said first organic liquid electrically conductive.

3. The process of claim 2, wherein said ionic liquid has a cation and a counterion, and wherein said cation is selected from the group consisting of pyridinium, pyridazinium, pyrimidinium, pyrazinium, imidazolium, pyrazolium, thiazolium, oxazolium, triazolium, and derivatives thereof, and wherein said counterion is an anionic detergent.

4. The process of claim 2, wherein said ionic liquid has a cation and a counterion, and wherein said cation is selected from the group consisting of pyridinium, pyridazinium, pyrimidinium, pyrazinium, imidazolium, pyrazolium, thiazolium, oxazolium, triazolium, and derivatives thereof, and wherein said counterion is an anionic detergent.

5. The process of claim 4, wherein said counterion is selected from the group consisting of decylsulfate and dodecylsulfate.

6. The process of claim 2, wherein said first organic liquid comprises an electrically non-conductive organic liquid and an ionic liquid having the formula $A^{30}X^{31}$ wherein $X^-$ is $YR_7$ where Y is an anionic group selected from the group consisting of $-SO_4^-$, $-PO_4^-$, $-CO_2^-$ and $R_7$ is an alkyl or alkenyl group having about 6 to about 20 carbon atoms, and $A^-$ is an organic cation capable of binding with $X^-$ to form an ionic liquid that is liquid at or near room temperature.

7. The process of claim 2, wherein said first and second organic liquids include at least one ionic liquid having the formula $A^+X^-$ wherein $A^+$ is an organic cation and $X^-$ is the anion of an anionic detergent.

8. The process of claim 1 wherein said first and second organic liquids are the same.

9. The process of claim 1, wherein said first organic liquid is hydrophobic.

10. The process of claim 1, wherein said sample contains hydrophobic components to be separated by said electrophoresis process.

11. The process of claim 10, wherein said hydrophobic components are hydrophobic proteins.

12. The process of claim 10, wherein said hydrophobic components are membrane proteins.

13. The process of claim 1, wherein said electrophoresis gel is a capillary electrophoresis device and said separation process comprises separating said components by capillary electrophoresis.

14. The process of claim 1, wherein said first organic liquid comprises an electrically non-conductive organic liquid and an ionic liquid having the formula $A^+X^-$ wherein $A^+$ is selected from the group consisting of pyridinium, pyridazinium, pyrimidinium, pyrazinium, imidazolium, pyrazolium, thiazolium, oxazolium, triazolium, and derivatives thereof, and $X^-$ is selected from the group consisting of $(CF_3)_2PF_4^-$, $(CF_3)_3PF_3^-$, $(CF_3)_4PF_2^-$, $(CF_3)_5PF^-$, $(CF_3)_6P^-$, $SF_5CF_2SO_3^-$, $SF_5CHFCF_2SO_3^-$, $SP_3CF_2(CF_3)_2CO^-$, $(CF_3SO_2)_2CH^-$, $(SF_5)_3C^-$, $(O(CF_3)_2C_2(CF_3)_2O)_2PO^-$, $Cl^-$, $F^-$, $BF_4^-$, $PF_6^-$, $AsF_6^-$, $CF_3SO_3^-$, $NO_3^-$, $AlCl_4^-$, and $Al(OH)_2Cl_2^-$, and $YR_7$ where Y is an anionic group selected from the poop consisting of $-SO_4^-$, $-PO_4^-$, $-CO_2^-$ and $R_7$ is an alkyl or alkenyl group having about 6 to about 20 carbon atoms, and mixtures thereof.

15. The process of claim 1, wherein said first organic liquid comprises an electrically non-conductive organic liquid and about 0.1% to about 2.0% by volume of an ionic liquid.

16. The process of claim 15, wherein said second organic liquid comprises an electrically non-conductive organic liquid and about 0.1% to about 2.0% by volume of an ionic liquid.

17. A process for electrophoretic separation of proteins, said process comprising the steps of:

providing an electrophoresis substrate for the electrophoretic separation of molecules, said electrophoresis substrate having a first end and a second end and a protein sample at said first end and a non-aqueous electrically conductive liquid in contact with said first and second ends of said electrophoresis substrate, and applying an electric current between said first end and second end of said electrophoresis substrate to cause said proteins in said sample to migrate through said substrate and to electrophoretically separate proteins from said sample wherein said electrically conductive liquid is substantially absent of water.

18. The process of claim 17, wherein said electrophoresis substrate is a capillary electrophoresis device and said process comprises separating said proteins by capillary electrophoresis.

19. The process of claim 17, wherein said proteins are membrane proteins.

20. The process of claim 17, wherein said electrically conducting liquid comprises an organic solvent containing an electrolyte in an amount to render said organic solvent electrically conducting.

21. The process of claim 17, wherein said electrophoresis substrate is an electrophoresis gel that is compatible with said electrically conducting liquid.

22. The process of claim 21, wherein said electrophoresis gel is an electrophoresis gel tube and said process comprises separating said proteins through said electrophoresis gel tube.

23. The process of claim 21, wherein said electrophoresis gel is an electrophoresis gel slab.

24. The process of claim 17, wherein said proteins are hydrophobic proteins.

25. A process for electrophoretic separation of proteins, said process comprising the steps of:

providing an electrophoresis substrate for the electrophoretic separation of molecules, said electrophoresis substrate having a first end and a second end and a protein sample at said first end and a non-aqueous electrically conductive liquid in contact with said first and second ends of said electrophoresis substrate, and applying an electric current between said first end and second end of said electrophoresis substrate to cause said proteins in said sample to migrate through said substrate and to electrophoretically separate proteins from said sample, wherein said electrically conducting liquid comprises an organic solvent and an ionic liquid in an amount sufficient to render said organic solvent sample electrically conducting.

26. The process of claim 22, wherein said electrically conducting liquid comprises about 0.1% to about 2.0% by volume of said ionic liquid.

27. The process of claim 25, wherein said ionic liquid has the formula $A_+X^-$ wherein $A^+$ is selected from the group consisting of pyridinium, pyridazinium, pyrimidinium, pyrazinium, imidazolium, pyrazolium, thiazolium, oxazolium, triazolium, and derivatives thereof, and $X^-$ is selected from the group consisting of $(CF_3)_2PF_4^-$, $(CF_3)_3PF_3^-$, $(CF_3)_4PF_2^-$, $(CF_3)_5PF^-$, $(CF_3)_6P^-$, $SF_3CF_2SO_3^-$, $SF_5CHFCF_2SO_3^-$, $SF_3CF_2(CF_3)_2CO^-$, $(CF_3SO_2)_2CH^-$, $(SH_5)_3CH^-$, $(O\ (CF_3)_2C_2(CF_3)_2O)_2PO^-$, $Cl^-$, $F^-$, $BF_4^-$, $PF_6^-$, $AsF_6^-$, $CF_3SO_3^-$, $NO_3^-$, $AlCl_4^-$, and $Al(OH)_2Cl_2^-$.

28. The process of claim 25, wherein said ionic liquid has the formula $A^+Z^-$ wherein $A^+$ is selected from the group consisting of pyridimium, pyridazinium, pyrimidinium, pyrazinium, imidazolium, pyrazolium, thiazolium, oxazolium, triazolium, and derivatives thereof, and $Z^-$ is an anionic detergent anion.

29. The process of claim 25, wherein said electrically conducting liquid includes at least one ionic liquid having the formula $A^-Z^+$ wherein $A^+$ is an organic cation and $Z^-$ is an anionic detergent.

30. The process of claim 29, where $Z^-$ has the formula $YR_7$ wherein Y is an anionic group selected from the group consisting of $-SO_4^-$ and $-CO_2^-$ and $R_7$ is an alkyl or alkenyl group having about 6 to about 20 carbon atoms.

31. The process of claim 30, wherein $Z^-$ is selected from the group consisting of decylsulfate and dodecylsulfate.

32. An electrophoresis gel substrate comprising:

a polymeric gel material having a dimension sufficient to separate macromolecules by electrophoresis; and an organic liquid dispersed in said polymer gel material to form said gel substrate, said organic liquid containing an electrolyte in an amount sufficient to electrophoretically separate macromolecules through said gel, and where said organic liquid is compatible with said polymeric gel material to form a stable gel and wherein said gel material and said organic liquid are substantially absent of water wherein said organic liquid, includes at least one organic solvent selected from the group consisting of alcohols, ketones, nitriles, alkanes, alkenes, cycloalkanes, cycloalkenes, aromatic compounds, heterocyclic compounds, and mixtures thereof or wherein said gel material is selected from the group, consisting of polyurethanes and polyurea-urethanes.

33. The gel substrate of claim 32, further comprising a rigid support having an open first end and an open second end for supporting said gel material.

34. The gel substrate of claim 33, wherein said rigid support is a tube having a length and a diameter sufficient for electrophoresis separation.

35. The gel substrate of claim 33, wherein said rigid support comprises two planar support members supporting said gel material therebetween, and wherein said planar support members have a dimension sufficient for electrophoresis separation.

36. The gel substrate of claim 32, wherein said organic liquid is a substantially non-electrically conducting organic liquid and where said electrolyte is included in an amount to render said organic liquid electrically conducting.

37. The gel substrate of claim 32, wherein said organic liquid is an ionic liquid.

38. The gel substrate of claim 37, wherein said ionic liquid includes at least one ionic liquid having the formula $A^+Z^-$ wherein $Z^-$ is $YR_7$ wherein Y is an anionic group selected from the group consisting of $-SO_4^-$ and $-CO_2^-$, and $R_7$ is an alkyl or alkenyl group having about 6 to about 20 carbon atoms, and $A^+$ is an organic cation capable of binding with $Z^-$ to form an ionic liquid that is liquid at or near room temperature.

39. The gel substrate of claim 32, wherein said organic liquid has an affinity to solubilize hydrophobic compounds.

40. The gel substrate of claim 32, wherein said organic liquid has an affinity to solubilize membrane proteins.

41. The gel substrate of claim 32, wherein said polymeric gel is made from a crosslinked isocyanate end-capped urethane prepolymer.

42. The gel substrate of claim 41, wherein said prepolymer is crosslinked agent is a diamine.

43. The gel substrate of claim 32, wherein said organic liquid includes an organic solvent containing about 0.1% to about 2.0% by volume of an ionic liquid based an the volume of said organic solvent.

44. An electrophoresis gel substrate comprising:
a polymeric gel material having a dimension sufficient to separate macromolecules by electrophoresis; and
an organic liquid dispersed in said polymer gel material to form said gel substrate, said organic liquid containing an electrolyte in an amount sufficient to electrophoretically separate macromolecules through said gel, and where said organic liquid is compatible with said polymeric gel material to form a stable gel, wherein said electrolyte is an ionic liquid in an amount sufficient to render said organic liquid electrically conducting for electrophoretic separation.

45. The gel substrate of claim 44, wherein said ionic liquid has the formula $A^+X^-$ wherein $A^+$ is selected from the group consisting of pyridinium, pyridazinium, pyrimidinium, pyrazinium, imidazolium, pyrazolium, thiazolium, oxazolium, triazolium, and derivatives thereof, and $X^-$ is selected from the group consisting of $(CF_3)_2PF_4^-$, $(CF_3)_3PF_3^-$, $(CF_3)_4PF_2^-$, $(CF_3)_5PF^-$, $(CF_3)_6P^-$, $SF_3CF_2SO_3^-$, $SF_5CHFCF_2SO_3^-$, $SF_3CF_2(CF_3)_2CO^-$, $(CF_3SO_2)_2CH^-$, $(SF_5)_3C^-$, $(O(CF_3)_2C_2(CF_3)_2O)_2PO^-$, $Cl^-$, $F^-$, $BF_4^-$, $PF_6^-$, $AsF_6^-$, $CF_3SO_3^-$, $NO_3^-$, $AlCl_4^-$, and $Al(OH)_2Cl_2^-$.

46. An ionic liquid having the formula $$A^+Z^-$$

where $A^-$ is an organic cation and $Z^-$ is an having 10 to 22 carbon atoms, anionic surfactant properties, and where said ionic liquid is liquid at room temperature.

47. The ionic liquid of claim 46, wherein $A^+$ is selected from the group consisting of pyridinium, pyridazinium. pyrimidinium, pyrazinium, imidazolium, pyrszolium, thiazolium, oxazolium, triazolium, and derivatives thereof and $Z^-$ is an anion of an anionic detergent.

48. The ionic liquid of claim 46, wherein $Z^-$ is selected from the group consisting of decylsulfate and dodecylsulfate.

49. The ionic liquid of claim 46, wherein $Z^-$ has the formula $YR_7$, where Y is selected from the group consisting of carboxylate, sulfonate and phosphate, and $R_7$ is an alkyl or alkenyl.

50. The ionic liquid of claim 49, wherein $R_7$ is a $C_6$ to $C_{22}$ alkyl or alkenyl.

51. An electrophoresis separation process for separating a sample into its components, said process comprising the steps of:
providing an electrophoresis substrate having a first end and a second end, a sample in contact with said substrate, a first electrically conductive organic liquid containing an ionic liquid at said first end, a second electrically conductive organic liquid at said second end, and
applying an electric potential between said first end and said second end of said substrate to cause said components in said sample to migrate through said substrate from said first end toward said second end and electrophoretically separating components of said sample
wherein said ionic liquid has the formula $$A^+Z^-$$

where $A^+$ is an organic cation and $Z^-$ is an anion having anionic surfactant properties, and where said ionic liquid is liquid at room temperature.

52. The electrophoresis separation process of claim 51 wherein $A^-$ is selected from the group consisting of pyridinium, pyridazinium, pyrimidinium, pyrazinium, imidazolium, pyrazolium, thiazolium, oxazolium, triazolium, and derivatives thereof and $Z^-$ is an anion of an anionic detergent.

53. The electrophoresis separation process of claim 51 wherein $Z^-$ selected from the group consisting of decylsulfate and dodecylsulfate.

54. The electrophoresis separation process of claim 51 wherein $Z^-$ has the formula $YR_7$, where Y is selected from the group consisting of carloxylate, sulfonate and phosphate, and $R_7$ is an alkyl or alkenyl.

55. The electrophoresis separation process of claim 54 wherein $R_7$ is a $C_6$ to $C_{22}$ alkyl or alkenyl.

56. The electrophoresis separation process of claim 54 wherein $R_7$ is an alkyl having at least 6 carbon atoms.

* * * * *